(12) United States Patent
Van Herpen et al.

(10) Patent No.: US 7,615,760 B2
(45) Date of Patent: Nov. 10, 2009

(54) LUMINESCENCE SENSOR COMPRISING AT LEAST TWO WIRE GRIDS

(75) Inventors: Maarten Marinus Johannes Wilhelm Van Herpen, Eindhoven (NL); Henk Van Houten, Eindhoven (NL); Derk Jan Wilfred Klunder, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 12/067,309

(22) PCT Filed: Sep. 18, 2006

(86) PCT No.: PCT/IB2006/053336

§ 371 (c)(1),
(2), (4) Date: Mar. 19, 2008

(87) PCT Pub. No.: WO2007/034395

PCT Pub. Date: Mar. 29, 2007

(65) Prior Publication Data

US 2008/0217558 A1    Sep. 11, 2008

(30) Foreign Application Priority Data

Sep. 22, 2005    (EP) .................................. 05108773

(51) Int. Cl.
    *G21H 3/02*    (2006.01)
(52) U.S. Cl. .................. 250/459.1; 250/458.1
(58) Field of Classification Search ............. 250/459.1, 250/458.1; 264/21
See application file for complete search history.

(56) References Cited

U.S. PATENT DOCUMENTS

| | | | | |
|---|---|---|---|---|
| 3,786,270 A * | 1/1974 | Borkowski et al. | ........ | 250/385.1 |
| 5,045,701 A * | 9/1991 | Goldstein et al. | ...... | 250/339.08 |
| 5,831,329 A * | 11/1998 | Marso et al. | ................. | 257/750 |
| 6,483,096 B1 | 11/2002 | Kunz | | |
| 7,256,466 B2 * | 8/2007 | Lieber et al. | ................. | 257/414 |
| 2002/0101659 A1 | 8/2002 | Hansen | | |
| 2004/0041617 A1* | 3/2004 | Snider et al. | ................. | 327/365 |
| 2005/0040345 A1* | 2/2005 | Bakker et al. | ............ | 250/492.2 |

FOREIGN PATENT DOCUMENTS

AU          52239 86 A     7/1987
JP        2003231520 A     8/2003

OTHER PUBLICATIONS

Liu, Yongdong et al "Fluorescence Enhancement from an Array of Subwavelength Metal Apertures" Optics Letters, vol. 28, No. 7, Apr. 1, 2003, pp. 507-509.
Liu, Yongdong et al "Fluorescence Transmission through 1-D and 2-D Periodic Metal Films" Optics Express, vol. 12, No. 16, Aug. 9, 2004, pp. 3686-3693.

* cited by examiner

*Primary Examiner*—Constantine Hannaher
*Assistant Examiner*—Faye Boosalis

(57) ABSTRACT

The present invention proposes a sub-wavelength luminescence sensor, such as e.g. a luminescence biosensor or a luminescence chemical sensor, comprising at least two wire grids (1, 2) positioned perpendicular with respect to each other. The luminescence sensor, in which the excitation radiation is efficiently used and the luminescence radiation is efficiently detected, has an improved signal-to-noise ratio and a separated excitation and luminescence radiation.

20 Claims, 4 Drawing Sheets

LUMINESCENCE SENSOR COMPRISING AT LEAST TWO WIRE GRIDS

The present invention relates to luminescence sensors, for example luminescence biosensors or luminescence chemical sensors, and to a method for the detection of luminescence radiation generated by one or more luminophores present in such a luminescence sensor. More particularly, the invention relates to luminescence sensors with a high signal-to-noise ratio.

Sensors are widely used for measuring physical attributes or physical events. They output a functional reading of that measurement as an electrical, optical or digital signal. That signal is data that can be transformed by other devices into information. A particular example of a sensor is a biosensor. Biosensors are devices that detect the presence (i.e. qualitative detection) or measure a certain amount (i.e. quantitative detection) of target molecules such as e.g. proteins, viruses, bacteria, cell components, cell membranes, spores, DNA, RNA, etc. in a fluid, such as for example blood, serum, plasma, saliva, . . . . The target molecules also are called the "analyte". In almost all cases, a biosensor uses a surface that comprises specific recognition elements for capturing the analyte. Therefore, the surface of the sensor device may be modified by attaching specific molecules to it, which are suitable to bind the target molecules which are present in the fluid.

For optimal binding efficiency of the analyte to the specific molecules, large surface areas and short diffusion lengths are highly favorable. Therefore, micro- or nano-porous substrates (membranes) have been proposed as biosensor substrates that combine a large area with rapid binding kinetics. Especially, when the analyte concentration is low (e.g. below 1 nM, or below 1 pM) the diffusion kinetics play an important role in the total performance of a biosensor assay.

The amount of bound analyte may be detected by luminescence, e.g. fluorescence. In this case the analyte itself may carry a luminescent, e.g. fluorescent, label, or alternatively an additional incubation with a luminescently, e.g. fluorescently, labelled second recognition element may be performed.

In prior art luminescent biosensors, there is a problem in separating the excitation and luminescence radiation, e.g. fluorescence radiation, because these types of radiation have a similar wavelength For solving the above problem, a luminescence sensor using sub-wavelength apertures or slits operating inside a fluid with sub-wavelength spatial resolution was proposed. In simple terms, excitation radiation is reflecting on the sub-wavelength apertures or slits, because they are too small to be seen by the radiation. This yields an evanescent field within the apertures or slits, which is used for exciting luminophores present in the apertures or slits. The luminescence that is generated exits the apertures or slits on the side opposed to the one that is irradiated, i.e. the excitation side, in that way separating excitation and luminescence radiation. Background luminescence generated on the excitation side of the apertures or slits is also suppressed by this (reflection) effect.

The problem with luminescence sensors using apertures is that the emitted luminescence needs to be able to exit the aperture, and therefore luminescence needs to be emitted close to the exit side of the aperture. This means that a significant amount of excitation radiation has already been suppressed, before it can ever generate luminescence, e.g. fluorescence, that is able to efficiently leave the aperture. In practice this means that the excitation radiation will be somewhat suppressed before it reaches the luminophore, e.g. fluorophore, in the aperture, and the generated luminescence, e.g. fluorescence, will also be somewhat suppressed before reaching the detector.

This problem can be solved by using a sensor with slits instead of apertures because one polarization is always able to travel through the slits, and therefore at least 50% of the generated luminescence, e.g. fluorescence, is always able to reach the detector side. The problem, however, with these kind of sensors is that also 50% of the generated background radiation is able to transmit through the slits.

It is an object of the present invention to provide a luminescence sensor, such as a luminescence biosensor or a luminescence chemical sensor, with an improved signal-to-noise ratio. It is a further object of the present invention to provide a method for the detection of luminescence radiation generated by one or more luminophores present in such a luminescence sensor. An advantage of the present invention can be that the excitation radiation is efficiently used and luminescence radiation is efficiently detected.

The above objectives are accomplished by a device and a method according to the present invention.

Particular and preferred aspects of the invention are set out in the accompanying independent and dependent claims. Features from the dependent claims may be combined with features of the independent claims and with features of other dependent claims as appropriate and not merely as explicitly set out in the claims.

The present invention provides a luminescence sensor, for example fluorescence sensor, comprising at least a first wire grid and a second wire grid. The first wire grid comprises slits and wires extending in a first direction and the second wire grid comprises slits and wires extending in a second direction, the first direction and the second direction being substantially perpendicular with respect to each other. According to the invention, when the sensor is irradiated with excitation radiation, e.g. excitation light, from an excitation radiation source, e.g. light source, the excitation radiation, e.g. excitation light, is polarized such that it is substantially suppressed by one of the at least first and second wire grid and is substantially not suppressed by the other of the at least first and second wire grid.

According to a preferred embodiment of the invention, the polarization of the excitation radiation, e.g. excitation light, may be such that it is substantially suppressed by the second wire grid which is positioned farthest away from the excitation radiation source, e.g. light source, and substantially not suppressed by the first wire grid which is positioned closest to the excitation radiation source, e.g. light source.

The luminescence sensor according to the invention has some advantages over the prior art sensors. For the luminescence sensor according to the invention, the excitation volume, i.e. the volume between the wires where luminescence is generated, is very small, i.e. below the diffraction limit, in at least two dimensions. This is achieved because the combination of the two wire grids forms sub-wavelength apertures. Another advantage is that the luminescence sensor according to the invention, if used in transmission mode, i.e. with the excitation radiation source on one side of the sensor and a detector at the other side, provides automatic separation of excitation radiation, e.g. excitation light, and luminescence, e.g. fluorescence, radiation. Moreover, in that case, background luminescence, e.g. fluorescence, generated at the side of the sensor opposite to the side on which a detector is positioned is unable to transmit through the apertures formed by the position of the first and second wire grid, thus improving the signal-to-background ratio. The luminescence sensor according to the invention is easy to align and to use and luminescence, e.g. fluorescence, radiation can efficiently reach the detector which also means that excitation can be done efficiently.

According to embodiments of the invention, the second wire grid may have a top surface and the first wire grid may be positioned on top of the second wire grid.

According to embodiments of the invention, a gap may be present between the first wire grid and the second wire grid, causing a distance d between the first and second wire grid. An advantage of these embodiments is that the full distance between the first and second wire grids can be used for excitation. This means that there is an increased excitation volume, which can be tuned by varying the distance between the wire grids.

According to an embodiment of the invention, the distance d may have any suitable value and may typically be between 100 nm and 100 µm, and may, according to other embodiments, optionally be variable by mounting wire grid 1 and wire grid 2 independent from each other.

According to an embodiment of the invention, the luminescence sensor may furthermore comprise a third wire grid which is aligned such that the wires of the third wire grid are positioned under or above the slits of respectively the first or second wire grid.

According to particular embodiments, the third wire grid may be positioned on the top surface of the second wire grid and may be aligned such that the wires of the third wire grid are positioned above the slits of the second wire grid.

In other embodiments according the invention, the third wire grid may be positioned at the bottom surface of the first wire grid and may be aligned such that the wires of the third wire grid are positioned under the slits of the first wire grid.

According to embodiments of the invention, the luminescence sensor may furthermore comprise a gap between the first wire grid and the third wire grid or between the third wire grid and the second wire grid.

The slits may have a smallest dimension and the sensor may be for being immersed in an immersion fluid. According to embodiments of the invention, the smallest dimension of the slits may be smaller than the wavelength of the excitation radiation in the immersion fluid.

According to embodiments of the invention, at least one of the at least first and second wire grid may be positioned on top of a bearing substrate.

According to the embodiments of the invention, the luminescence sensor may be a fluorescence sensor. In particular embodiments, the luminescence sensor may be a luminescence biosensor, e.g. a fluorescence biosensor.

The present invention furthermore provides a method for the detection of luminescence, e.g. fluorescence, radiation generated by at least one luminophore, e.g. fluorophore. The method comprises irradiating a luminescence, e.g. fluorescence, sensor with excitation radiation, e.g. excitation light, the luminescence, e.g. fluorescence, sensor comprising at least a first wire grid having slits and wires extending in a first direction and a second wire grid having slits and wires extending in a second direction, the first and second direction being substantially perpendicular with respect to each other. According to the method of the invention, the excitation radiation, e.g. excitation light, coming from an excitation radiation source is polarized such that it is not substantially suppressed by one of the at least first and second wire grid and is substantially suppressed by the other of the at least first and second wire grid.

According to an embodiment of the invention, the polarization of the excitation radiation, e.g. excitation light, not substantially suppressed by the first wire grid which is closest to the excitation radiation source but is substantially only suppressed by the second wire grid which is farthest away from the excitation radiation source.

The method according to the invention may, according to embodiments, furthermore comprise detecting generated luminescence, e.g. fluorescence, radiation.

The above and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

Figure 1:
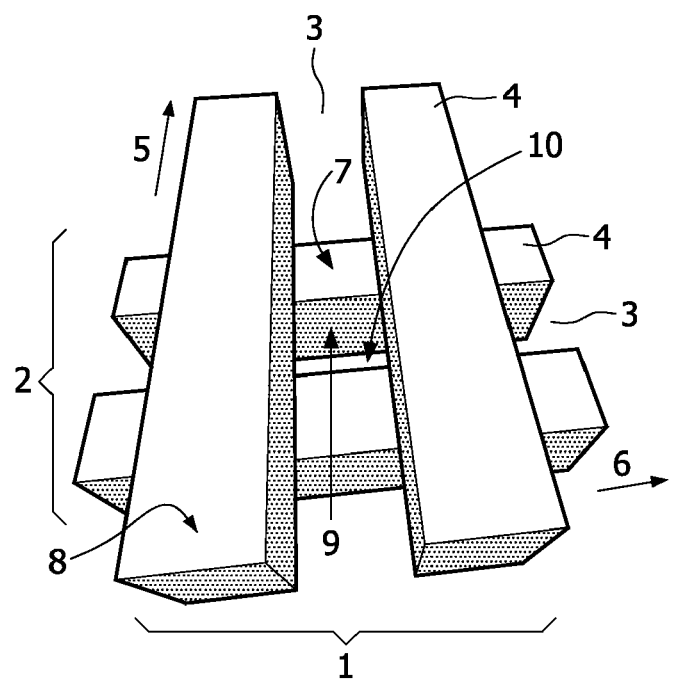
FIG. 1 to 3 illustrate different views (respectively perspective view, perspective top view and perspective bottom view) of a luminescence sensor according to a first embodiment of the invention.

In the different figures, the same reference signs refer to the same or analogous elements.

The present invention will be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

The present invention provides a qualitative or quantitative sensor, more particularly a luminescence sensor, which may for example be a luminescence biosensor or luminescence chemical sensor, which shows good signal-to-background ratio, as well as a method for the manufacturing of such a luminescence sensor. A luminescence sensor according to the present invention comprises at least a first wire grid 1 and a second wire grid 2. The wire grids 1, 2 are formed in a substrate as a network of slits 3, the slits 3 preferably being uniformly spaced apart. This may be obtained by applying conventional techniques known by persons skilled in the art, such as, for example, E-beam lithography or laser interference lithography. The remaining parts of the substrate form wires 4. The substrate may, for example, be a metal substrate, e.g. a gold substrate, or a semiconductor substrate, e.g. a silicon substrate. In the description hereinafter, with substrate is meant the material from which the wire grids 1, 2 are formed, also called the wire grid material.

According to an aspect of the present invention, in the first wire grid 1 the slits 3 extend in a first direction and in the second wire grid 2 the slits 3 extend in a second direction, the first and second direction being substantially perpendicular with respect to each other. The sensor according to embodiments of the present invention, comprising such crossed first and second wire grids 1, 2 is irradiated with excitation radiation which is polarized such that it is not suppressed by the first wire grid 1, but is suppressed by the second wire grid 2.

In a first embodiment of the invention, the luminescence sensor, e.g. fluorescence sensor, comprises a first wire grid 1 formed in a first substrate and a second wire grid 2 formed in a second substrate. The first and second substrates, or in other words, the wire grid materials used to respectively form the first and second wire grids 1, 2, may, for example, both be metal substrates, e.g. gold substrates or materials, or both be semiconductor substrates or materials, e.g. silicon substrates or materials, or the first (or second) substrate or material may be a metal while the second (or first) substrate or material may be a semiconductor material. The first substrate, and thus the first wire grid 1, and the second substrate, and thus the second wire grid 2, may have, according to embodiment of the invention, the same thickness, but may, in other embodiments, also have a different thickness. The thickness of the first and second wire grid 1, 2 may typically be substantially the same as the width of the slits 3, which according to embodiments of the invention, may be smaller than the wavelength of excitation radiation in the medium which fills the slits. However, the performance of the wire grids 1, 2 improves if its thickness is larger than this wavelength. Therefore, the thickness of the wire grids 1, 2 may be between 100 and 1000 nm. The medium which fills the slits may be a liquid or a gas, but may also be vacuum comprising at least one luminescent particle to be detected. In use the sensor may be immersed in the medium, e.g. in a liquid medium, or the slits may be filled with the medium in any other suitable way, e.g. by means of a micropipette in case of a liquid medium, or e.g. by spraying a gas over the sensor and into the slits.

The first wire grid 1 alternately comprises slits 3 and wires 4 extending in a first direction which is indicated by arrow 5 in FIG. 1, and a second wire grid 2, alternately comprising slits 3 and wires 4 extending in a second direction which is indicated by arrow 6 in FIG. 1, the first direction 5 and the second direction 6 being substantially perpendicular with respect to each other. The slits 3 may have a smallest dimension which preferably is smaller than the wavelength of the excitation radiation in the medium in which the sensor is immersed or with which the slits are filled. Preferably slits 3 may have a smallest dimension which is smaller than half the wavelength of the excitation radiation in the fluid in which the sensor is immersed or the medium with which the slits are filled.

In this first embodiment of the invention, the first wire grid 1 is positioned at a top surface 7 of the second wire grid 2. The sensor is irradiated through the top surface 8 of the first wire grid 1.

Figure 2:
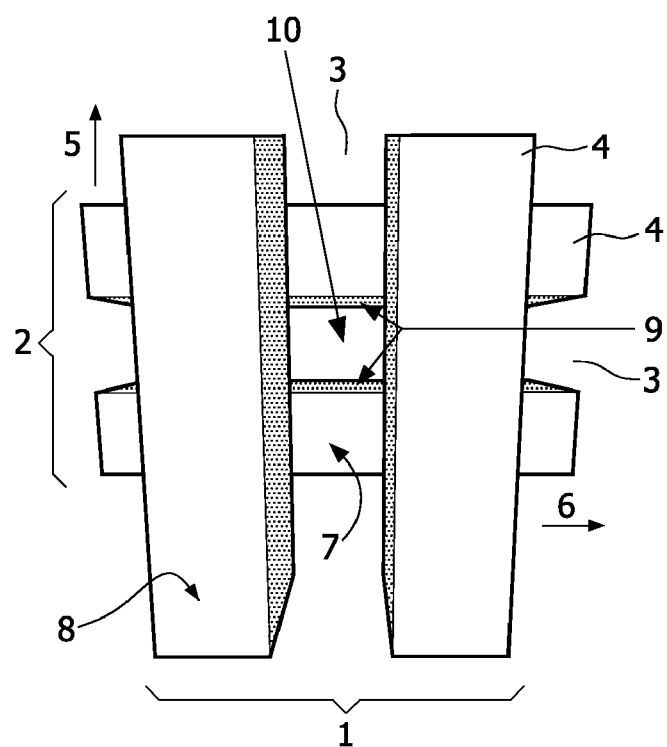
Figure 3:
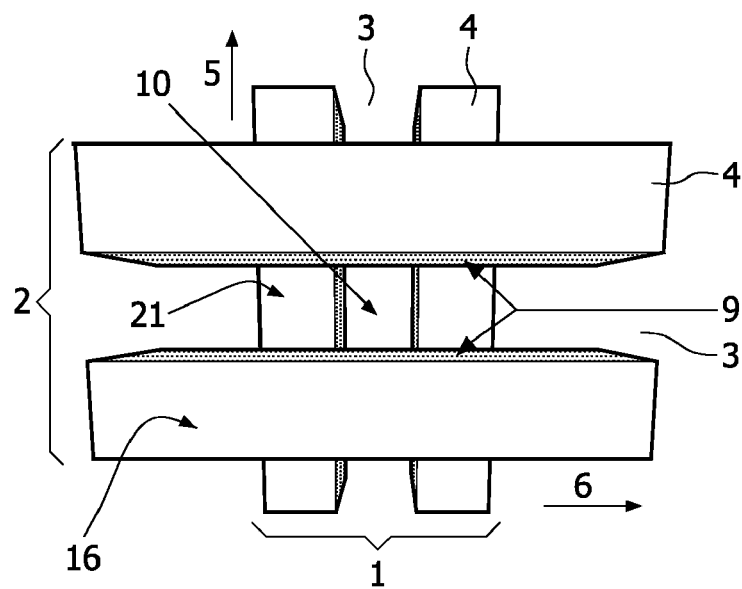

The configuration of the first and second wire grid 1, 2 according to the first embodiment is illustrated in FIG. 1, FIG. 2 (top view) and FIG. 3 (bottom view). Luminophores, for example fluorophores, may preferably be attached to the second wire grid 2 which is located farthest away from the excitation radiation source (see further) in the slits 3 of the second wire grid 2, at those sides of the wires 4 of the second wire grid 2 indicated by reference number 9 in FIG. 1 to 3. In that way they are closer to a detector for detecting luminescence radiation coming from the luminophores, e.g. fluorescence from fluorophores, and further away from an excitation source, for example a light source, for irradiating the sensor with excitation irradiation, for example excitation light. According to the invention, the irradiation source, for example light source, may preferably be positioned at a first side of the luminescence sensor while the detector may preferably be positioned at a second side of the luminescence sensor, the first and second side being opposite to each other with respect to the luminescence sensor. Luminescence generated at the first wire grid 1 has to transmit through the combination of the first and second wire grid 1, 2 and this means it will be suppressed. Therefore, the luminophores, e.g. fluorophores, should preferably be attached to the second wire grid 2 closest to the detector.

The combination of the first wire grid 1 and the second wire grid 2 as in the first embodiment leads to the formation of apertures 10 having a depth being equal to the sum of the thicknesses of the first wire grid 1 and the second wire grid 2.

Figure 4:
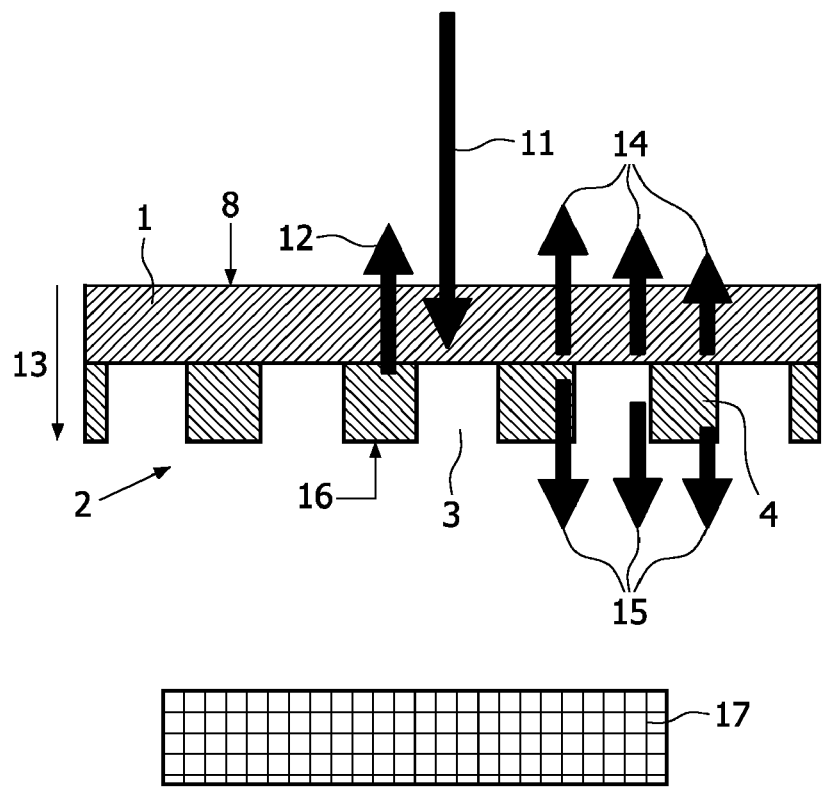
FIG. 4 illustrates the basic principle of the luminescence sensor according to the first embodiment of the invention.

In FIG. 4, the basic principle of the luminescence sensor according to the first embodiment of the invention is illustrated. Excitation radiation 11, for example excitation light, is illuminating the sensor through the top surface 8 of the first wire grid 1.

Wire grids 1, 2 have a polarization dependent suppression. Transmission of radiation through a wire grid 1, 2 shows, similar to a single slit 3, a strong polarization dependence: transmission for TE polarization state (E field parallel to the slits) is significantly lower than for TM polarization state. The intensity distribution for TM polarized radiation inside the wire grid 1, 2 is a standing wave pattern which indicates a Fabry-Perot effect; this is also supported by the stronger maximum normalized intensity for a slit height of 600 nm, i.e. the resonant effect. Behind the wire grid 1, 2, the intensity rapidly drops which is attributed (like for TE polarization) to divergence in the free space behind the wire grid 1, 2.

The excitation radiation 11, for example excitation light, coming from an excitation radiation source (not shown in the figures), e.g. a light source, may preferably be polarized such that it is not substantially suppressed, or not suppressed at all, by the first wire grid 1, but is substantially only suppressed by the second wire grid 2. For example, for TM polarized excitation radiation, e.g. TM polarized excitation light, with the electrical field E perpendicular to the slits 3 in the first wire grid 1, the excitation radiation will pass through the first wire grid 1. According to the present invention, the two wire grids 1, 2 are perpendicular. This means that one wire grid 1, 2 passes TM and the other wire grid 1, 2 passes TE polarized excitation radiation, e.g. TE polarized excitation light. If the first wire grid 1 is aligned to have little or no suppression for the excitation radiation, e.g. excitation light, then this means that the excitation radiation, e.g. excitation light, has TM polarization in a direction aligned with respect to the slits 3 in wire grid 1. Consequently, the excitation radiation, e.g. excitation light, has TE polarization aligned with the slits 3 in wire grid 2 and therefor wire grid 2 will substantially suppress the excitation radiation, e.g. excitation light. The suppression is achieved either by absorption or by reflection, the latter resulting in a reflected beam 12 as indicated in FIG. 4. The intensity of the excitation radiation 11, e.g. excitation light, only decreases within wire grid 2 in the direction indicated by arrow 13. The excitation radiation 11, for example excitation light, can be in the form of a broad beam, but can also be in the form of a multi-spot light source, in order to illuminate the open areas of the wire grids 1, 2, i.e. in particular the apertures 10, more efficiently. If, on the other hand, the polarization direction of radiation emitted by the excitation radiation source is not perfectly aligned with the slits of the first wire grid 1, then the first wire grid 1 blocks part of the excitation radiation, e.g. excitation light. This is not a problem for the operation of the luminescence sensor, however, a smaller amount of excitation radiation, e.g. excitation light, is in this case available for generation of luminescence, e.g. fluorescence. Hence, this will lead to a lower efficiency of the luminescence sensor, as the detector will only be able to detect less generated luminescence.

Luminophores, for example fluorophores, may, as already mentioned above, preferably be attached to the second wire grid 2 at the sides of the wires indicated by reference number 9 in FIGS. 1 to 3. Luminescence, for example fluorescence, that is generated in this area will only encounter the second wire grid 2. This means that, when a random polarization of the excitation radiation is assumed and thus there is 50% TE and 50% TM polarized light, at least 50% of the luminescence, for example fluorescence, passes through the second wire grid 2 and is not suppressed, i.e. the TM polarized light and a portion of the TE polarized light, because the TE polarized light is substantially suppressed, but a small amount may still transmit. This results in two beams of luminescence, for example fluorescence, both having a different polarization direction. These beams are indicated in FIG. 4 by arrows 14 and 15. Beam 15 leaves the sensor at the bottom side 16 of the second wire grid 2 where it is detected by a detector 17, for example a CCD or CMOS detector. Beam 14 leaves the sensor at the top surface 8 of the first wire grid 1.

In order to bring the luminophores, e.g. fluorophores to the preferred binding sites 9 at the second wire grid 2 of the luminescence sensor, a fluid comprising the luminophores needs to flow through the slits 3 of the wire grids 1, 2. This can be done in any of two directions as is illustrated in FIG. 5 by the arrows 18 and 19.

One possible fluid flow direction is indicated by arrow 18. The fluid is directly sent through the wire grids 1, 2 and flows in a direction perpendicular to the plane of the wire grids 1, 2. The advantage of using this fluid flow direction 18 is that it is simple to implement and that it has a relatively low flow resistance and thus allows more volume to be pumped through the wire grids 1, 2 per second.

Figure 5:
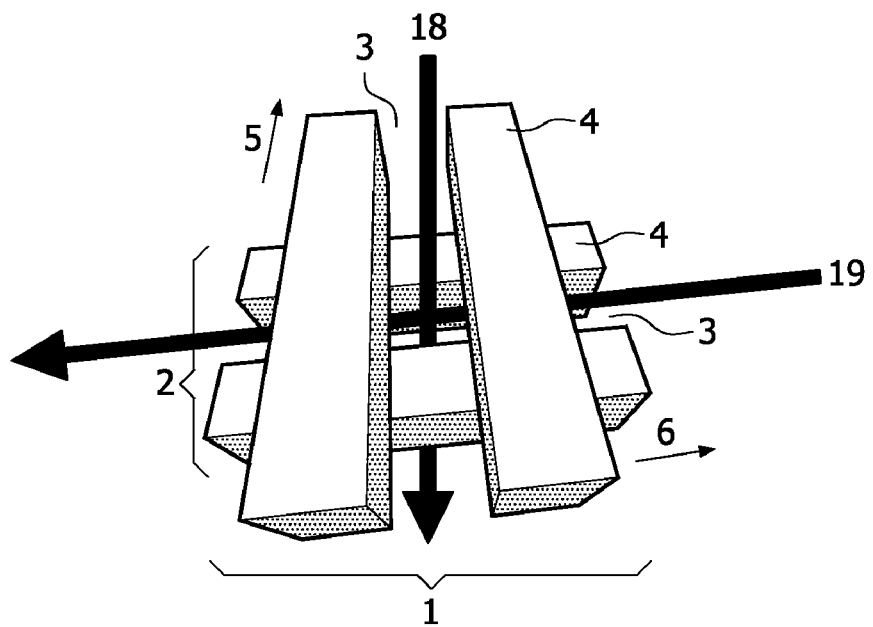
FIG. 5 illustrates possible fluid flow directions in the luminescence sensor according to the first embodiment of the invention.

Another possible fluid flow direction is in the plane of a wire grid, as indicated by arrow 19 in FIG. 5. In this case, the fluid flow goes through the slits 3 of, in the example given, the second wire grid 2. However, the fluid flow may also go through the slits 3 of the first wire grid 1. Thus, the fluid flows parallel to the wire grids 1, 2, in the slits 3 of one of the wire grids 1, 2. Preferably, the fluid flows parallel to and in the slits 3 of the second wire grid 2, if the second wire grid 2 is positioned under the first wire grid 1, as is the case in the sensor according to the first embodiment of the invention. There will be just a limited or not significant flow through the other wire grid, i.e. if the main fluid flow goes through the second wire grid 2, there will only be a minor flow through the first wire grid 1, because it is positioned perpendicular to the main direction of the flow as the slits 3 of both wire grids 1, 2 are positioned in planes which are substantially parallel with respect to each other. The advantage of this is that the most efficient binding of luminophores occurs in a region that has the most efficient luminescence, e.g. fluorescence, detection and excitation, i.e. on the sides of the wires 4 of the second wire grid 2, which is located closest to the detector 17.

Figure 6:
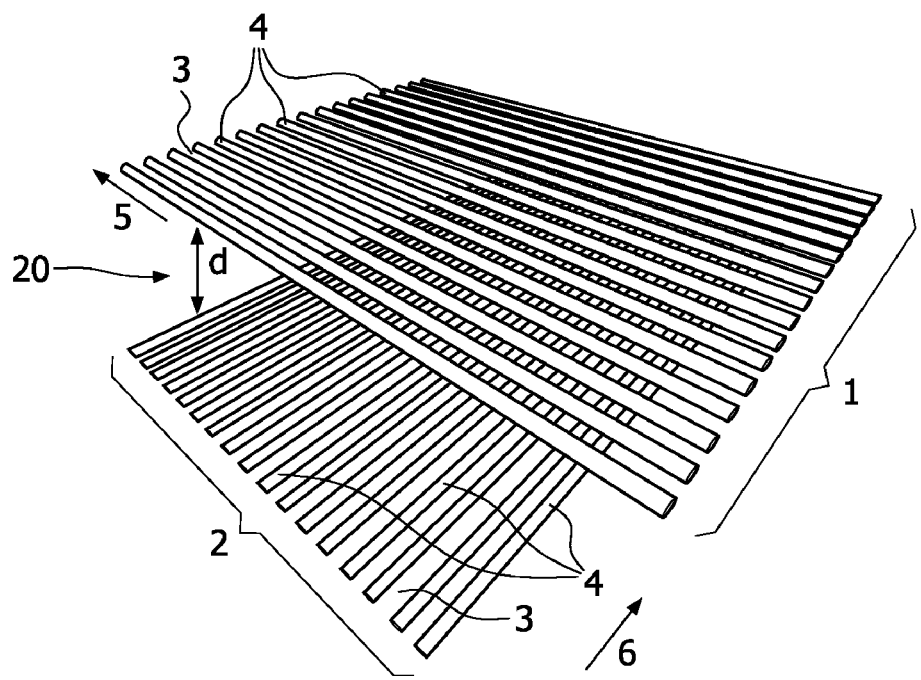
FIG. 6 illustrates a luminescence sensor according to a second embodiment of the invention.

In the above-described embodiment, the first wire grid 1 was positioned on the top surface 7 of the second wire grid 2. However, in some cases it can be advantageous that, in between the first wire grid 1 and the second wire grid 2, the luminescence sensor, e.g. fluorescence sensor, furthermore comprises a gap 20, causing a distance d between the first wire grid 1 and the second wire grid 2 (see FIG. 6). An example of such a case is where a larger luminescence, e.g. fluorescence, signal is needed because, for example, the luminescence, e.g. fluorescence, detector is not sensitive enough. Typically this may occur in applications where the concentration of luminophores, e.g. fluorophores, is somewhat lower, for example single-molecule detection.

Thus, in a second embodiment, the luminescence sensor, e.g. fluorescence sensor, again comprises a first wire grid 1 comprising slits 3 and wires 4 extending in a first direction 5 and a second wire grid 2 comprising slits 3 and wires 4 extending in a second direction 6, the first direction 5 and the second direction 6 being substantially perpendicular with respect to each other. The slits 3 may have a smallest dimension which may be smaller than the wavelength of the excitation radiation in the fluid the sensor is immersed in. The immersion fluid may be a liquid or a gas but may also be vacuum comprising at least one luminescent particle to be detected. The wire grids 1, 2 may be formed in a substrate by conventional techniques known by persons skilled in the art. The substrates may, for example, be metal substrates, e.g. gold substrates, or semiconductor substrates, e.g. silicon substrates. In between the first wire grid 1 and the second wire grid 2 a gap 20 is present causing a distance d between the first wire grid 1 and the second wire grid 2. The distance d may have any suitable value and may typically be between 100 nm and 100 μm, and may optionally be variable by mounting wire grid 1 and wire grid 2 independently from each other.

According to this second embodiment, luminophores, e.g. fluorophores, may, similar to the first embodiment, preferably be positioned at the second wire grid 2 or within the medium, e.g. fluid, filling the gap 20.

Figure 7:
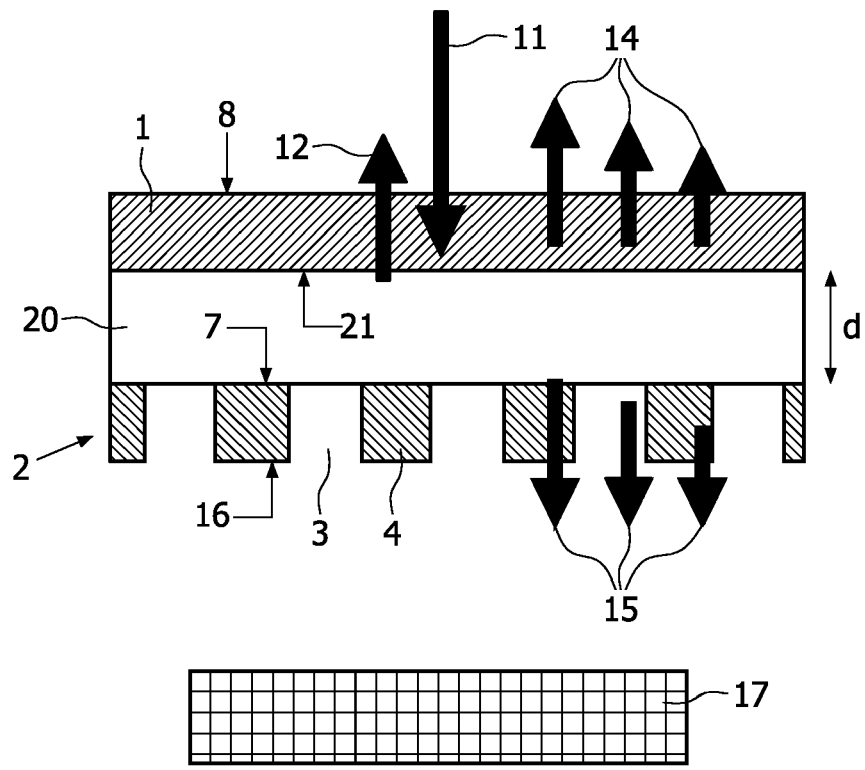
FIG. 7 illustrates the basic principle of the luminescence sensor according to the second embodiment of the invention.

In FIG. 7 the basic principle of the sensor configuration of the second embodiment is illustrated. This figure shows the first and second wire grids 1, 2 with the gap 20 present between the bottom surface 21 of the first wire grid 1 and the top surface 7 of the second wire grid 2, hence causing a distance d between the first wire grid 1 and the second wire grid 2. The sensor is irradiated with excitation radiation 11, e.g. excitation light, through the top surface 8 of the first wire grid 1. Similar to the first embodiment, the polarization of the excitation radiation 11, e.g. excitation light, may be such that it is not substantially suppressed, or not suppressed at all, by the first wire grid 1 and is thus substantially only suppressed by the second wire grid 2.

The advantage of this second embodiment is that the full distance between the wire grids 1, 2 can be used for excitation. This means that there is an increased excitation volume, which can be tuned by varying the distance between the wire grids 1, 2. As the excitation of luminescence, e.g. fluorescence, is occurring within the gap 20, the length of this gap determines the excitation volume. Therefore, the excitation volume can be tuned by varying the distance between the wire grids 1, 2. Luminophores, e.g. fluorophores, may be positioned in the gap 20 but it is also possible that the luminophores, e.g. fluorophores, are floating within the medium, e.g. fluid, that fills the gap 20.

In a third embodiment of the invention, the luminescence sensor, e.g. fluorescence sensor, furthermore comprises a third wire grid 22 formed of a transparent material, for example vitreous or glass-like materials. The third wire grid 22 is positioned between the first wire grid 1 and the second wire grid 2, the first wire grid 1 comprising slits 3 and wires 4 extending in a first direction 5 and the second wire grid 2 comprising slits 3 and wires 4 extending in a second direction 6, the first and second direction 5, 6 being substantially perpendicular with respect to each other. The slits 3 may have a smallest dimension which may be smaller than the wavelength of the excitation radiation 11 in the fluid the sensor is immersed in. The immersion fluid may be a liquid or a gas but may also be vacuum comprising at least one luminescent particle to be detected. The third wire grid 22 also comprises wires 4 and slits 3, which are aligned in such a way that the wires 4 of the third wire grid 22 are positioned under or above, parallel to and running in the same direction as the slits 3 of the first wire grid 1 respectively the second wire grid 2.

Figure 8:
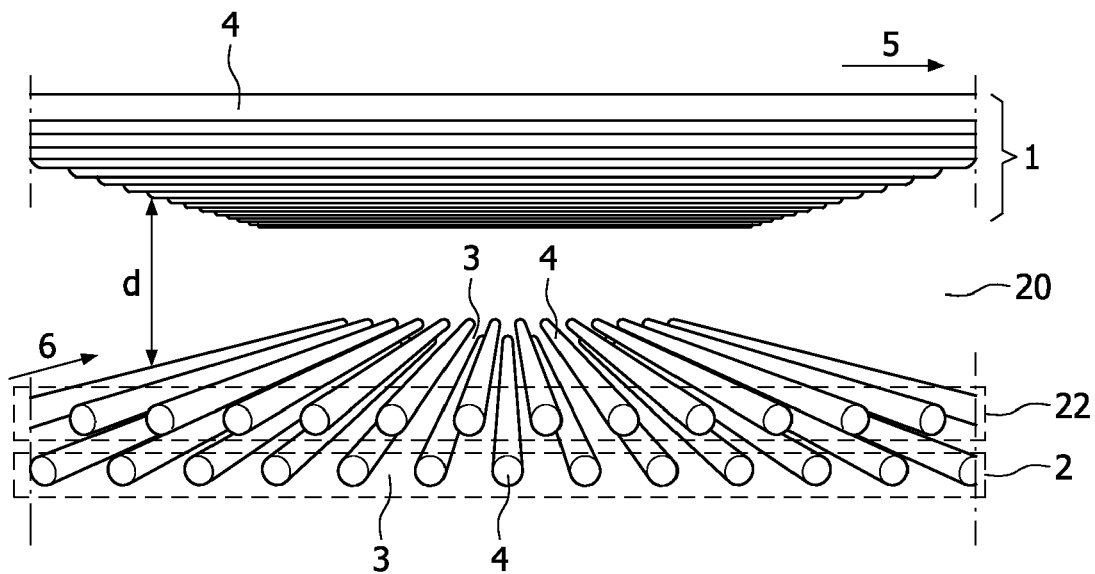
FIG. 8 illustrates a luminescence sensor according to a third embodiment of the invention.

In one possible implementation, as illustrated in FIG. 8, the third wire grid 22 may be positioned on top of the second wire grid 2 such that the wires 4 of the third wire grid 22 are positioned above the slits 3 of the second wire grid 2. A gap may be present between the second wire grid 2 and third wire grid 22. However, preferably the distance between the second wire grid 2 and the third wire grid 22 is as small as possible. Optionally, a gap 20 may be present between the first wire grid 1 and the third wire grid 22.

In a second possible implementation, not illustrated in the figures, the third wire grid 22 may be positioned at the bottom surface 21 of the first wire grid 1 such that the wires 4 of the third wire grid 22 are positioned under the slits 3 of the first wire grid 1, and run parallel thereto and in the same direction. According to embodiments of the invention, a gap may be present between the first wire grid 1 and the third wire grid 22. However, in other embodiment, there may be no gap between the first wire grid 1 and the third wire grid 22. Optionally, a gap 20 may be present between the third wire grid 22 and the second wire grid 2.

When the luminophores, e.g. fluorophores, are preferably bound to the third wire grid 22, the source of luminescence, e.g. fluorescence, is now placed at the location with optimized luminescence, e.g. fluorescence, excitation and detection. This is done because the excitation radiation, intensity and luminescence detection efficiency, is highest within the gap 20. The reason for using the third wire grid 22 is to give a method to place the luminophores, e.g. fluorophores, within the gap 20 between the wire grids. Hence, the main function of the third wire grid 22 is to provide binding sites for the luminophores, e.g. fluorophores, and to place these sites at the most suitable location. This results in a better sensitivity of the biosensor.

In the above-described embodiments, the wire grids 1, 2 are formed in a substrate. According to the invention, however, these wire grids 1, 2 may also be positioned on top of a bearing substrate (not shown in any of the figures). The bearing substrate may be made of a material that is transparent for the excitation radiation, e.g. excitation light, and the luminescence, e.g. fluorescence, radiation, in contrast with the wire grid material or substrate from which the wire grids are formed, which are made of a material that is non-transparent for the excitation radiation, e.g. excitation light, and the luminescence, e.g. fluorescence, radiation.

The luminescence sensor according to the invention has the following advantages over prior art luminescence sensors:

The excitation volume is very small, i.e. below the diffraction limit, in at least two dimensions. This is achieved because the combination of the two wire grids 1, 2 forms sub-wavelength apertures 10. In the depth some extra distance is achieved because the excitation radiation 11, e.g. excitation light, is not suppressed by the first wire grid 1 and because some of the luminescence, e.g. fluorescence, generated within this first wire grid 1 will be able to transmit to the second wire grid 2 and is then able to reach the detector 17. By small excitation volume is meant that, in practice, the slits 3 or apertures 10 formed by the combination of the first and second wire grid 1, 2 only transmit excitation radiation 11 into a small volume localized around the position of the aperture 10 or slit 3. This may be utilized for localized probing of the luminescence radiation 14, 15 and for minimizing the ratio of the luminescence radiation 14, 15 generated behind the aperture 10 or slit 3 and the luminescence radiation 14, 15 generated inside the aperture 10 or slit 3.

Automatic separation of excitation radiation 11 and luminescence, e.g. fluorescence, radiation 14, 15.

Background luminescence, e.g. fluorescence, generated at the side of the sensor opposite to the side on which a detector 17 is positioned is unable to transmit through the aperture 10, improving the signal-to-background ratio. Background luminescence, e.g. fluorescence, generated on the side of the combination of wire grids 1, 2 opposite to the detector side will need to travel through both wire grids 1, 2 and will therefore be suppressed.

Easy to align and use. Alignment is very simple, but the polarization of the excitation radiation 11 needs to be controlled. However, a small misalignment in the polarization may be allowed because it will only cause minor losses in the excitation radiation 11, e.g. excitation light, when travelling through the first wire grid 1. Assuming TE polarized excitation radiation, e.g. TE polarized light, is fully blocked, the transmittance of the wire grid 1, 2 may be determined by $(\cos(\text{angle of misalignment}))^2$.

Luminescence, e.g. fluorescence, can efficiently reach the detector 17 which also means that excitation can be done efficiently. According to the invention, at least 50% of the generated luminescence, e.g. fluorescence, is able to reach the detector side of the wire grids 1, 2, i.e. that side of the sensor at which a detector 17 is positioned. An additional advantage of this is that luminescence, e.g. fluorescence, generated at the top of the second wire grid 2 (where the excitation beam is the most intense) can reach the detector side just as easily. This means that next to more efficient luminescence, e.g. fluorescence, detection, also excitation can be done more efficiently.

It is to be understood that although preferred embodiments, specific constructions and configurations, as well as materials, have been discussed herein for devices according to the present invention, various changes or modifications in form and detail may be made without departing from the scope and spirit of this invention.

The invention claimed is:

1. A luminescence sensor comprising at least a first polarization wire grid and a second polarization wire grid for receiving and polarizing excitation radiation, wherein the first polarization wire grid comprises slits and wires extending in a first direction and the second polarization wire grid comprising slits and wires extending in a second direction, the first direction and the second direction being substantially perpendicular with respect to each other, wherein the excitation radiation is polarized such that it is substantially suppressed by one of the first and second polarization wire grids and substantially passed through by the other of the first and second polarization wire grids.

2. The luminescence sensor according to claim 1, wherein the sensor is irradiated with excitation radiation from an excitation radiation source.

3. The luminescence sensor according to claim 1, wherein the excitation radiation is polarized such that it is substantially suppressed by the second polarization wire grid which is positioned farthest away from the excitation radiation source and substantially not suppressed by the first polarization wire grid which is positioned closest to the excitation radiation source.

4. The luminescence sensor according to claim 1, the second polarization wire grid having a top surface, wherein the first polarization wire grid is positioned on the top surface of the second wire grid.

5. The luminescence sensor according to claim 1, wherein the luminescence sensor furthermore comprises a gap between the first polarization wire grid and the second polarization wire grid, causing a distance d between the first polarization wire grid and the second polarization wire grid.

6. The luminescence sensor according to claim 5, wherein the distance d is between 100 nm and 100 .mu.m.

7. The luminescence sensor according to claim 5, wherein the distance d is variable.

8. The luminescence sensor according to claim 1, wherein the luminescence sensor furthermore comprises a third wire grid between the first and second polarization wire grids and which is aligned such that the wires of the third wire grid are positioned under or above and parallel to the slits of respectively the first or second polarization wire grid.

9. The luminescence sensor according to claim 8, wherein the third wire grid is positioned on the top surface of the second polarization wire grid.

10. The luminescence sensor according to claim 8, wherein the third wire grid has side walls, the luminescence sensor comprising a luminophore attached on the side walls of the third wire grid.

11. The luminescence sensor according to claim 1, the slits having a smallest dimension and the sensor being immersed in an immersion fluid, wherein the smallest dimension of the slits is smaller than the wavelength of the excitation radiation in the immersion fluid.

12. The luminescence sensor according to claim 1, wherein at least one of the at least first and second polarization wire grids is positioned on top of a bearing substrate.

13. The luminescence sensor according to claim 1, wherein the luminescence sensor is a luminescence biosensor.

14. The luminescence biosensor according to claim 13, wherein the luminescence biosensor is a fluorescence biosensor.

15. The luminescence sensor according to claim 1, wherein the first and second polarization wire grids have side walls, the luminescence sensor comprising a luminophore attached on the side walls of one of the first and second polarization wire grids.

16. A method for the detection of luminescence radiation generated by at least one luminophore, the method comprising acts of:
    irradiating a luminescence sensor with excitation radiation, the luminescence sensor comprising at least a first polarization wire grid having slits and wires extending in a first direction and a second polarization wire grid having slits and wires extending in a second direction, the first direction and the second direction being substantially perpendicular with respect to each other; and
    polarizing luminescence radiation in the luminescence sensor,
    wherein the excitation radiation is polarized such that it is substantially suppressed by one of the at least first polarization wire grid and second polarization wire grid and substantially passed through by the other of the at least first polarization wire grid and second polarization wire grid.

17. The method according to claim 16, wherein the excitation radiation is substantially passed through by the first polarization wire grid but is substantially suppressed by the second polarization wire grid.

18. The method according to claim 16, comprising an act of detecting the generated luminescence radiation.

19. The method according to claim 16, wherein the first and second polarization wire grids have side walls, the method comprising an act of attaching a luminophore to the side walls of one of the first and second polarization wire grids.

20. The luminescence sensor according to claim 16, comprising acts of:
    providing a third wire grid having side walls, wherein the third wire grid is provided between the first an second wire grids; and
    attaching a luminophore to the side walls of the third wire grid.

* * * * *